Sept. 6, 1955 A. P. HOWARD Plant Pat. 1,417
ROSE PLANT
Filed Aug. 31, 1954
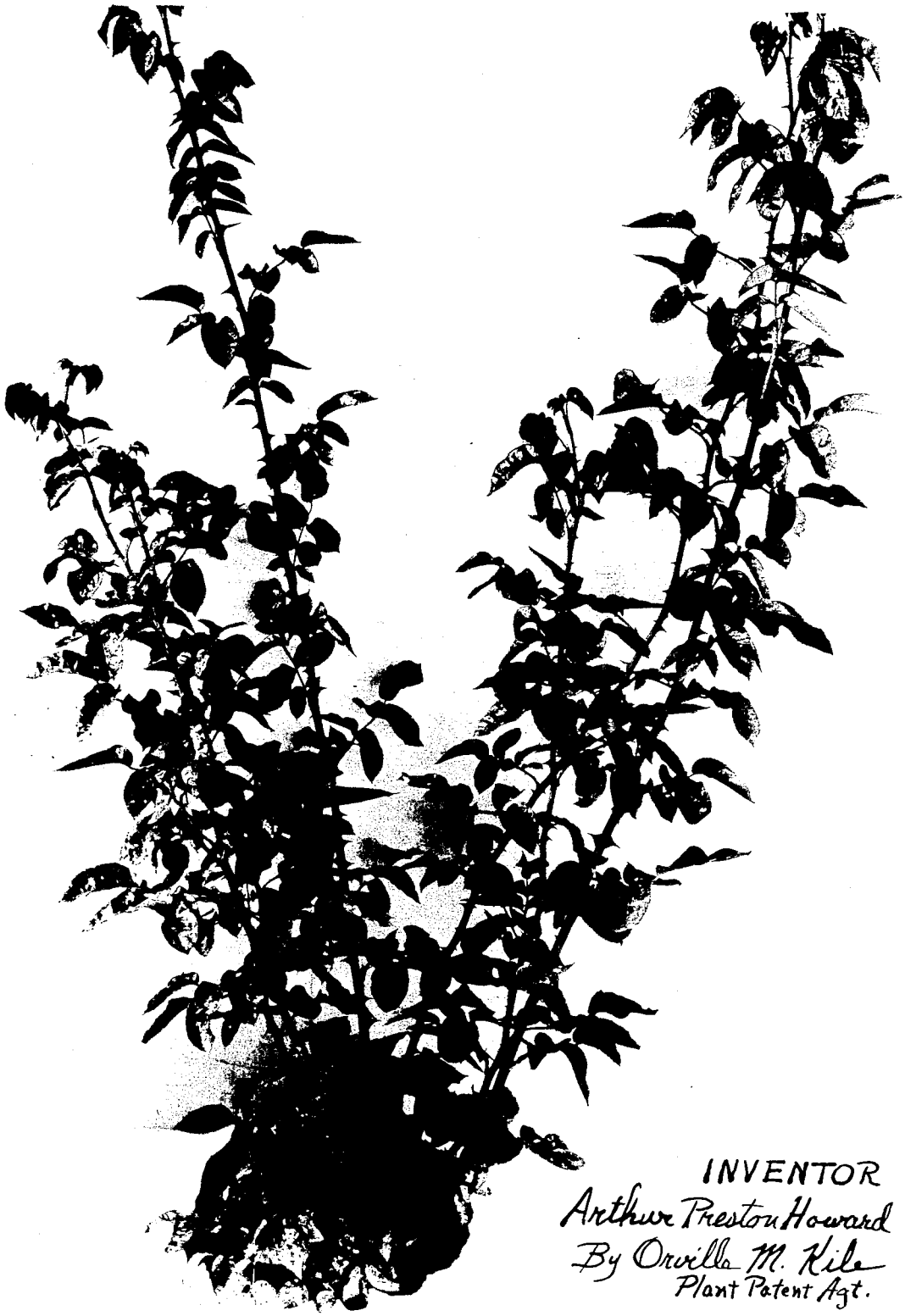
INVENTOR
Arthur Preston Howard
By Orville M. Kile
Plant Patent Agt.

United States Patent Office

Plant Pat. 1,417
Patented Sept. 6, 1955

1,417

ROSE PLANT

Arthur Preston Howard, Sierra Madre, Calif., assignor to Howard & Smith, Montebello, Calif.

Application August 31, 1954, Serial No. 453,451

1 Claim. (Cl. 47—61)

My present discovery pertains to a new hybrid tea rose plant, the outstanding novel feature of which is its climbing habit. In the course of my regular duties I discovered this new variety as a sport of the variety Fred Howard (Plant Patent No. 1,006) which was growing in the rose gardens of the company of which I am part owner. In most respects except the climbing habit the new variety is like its parent.

I have asexually reproduced this new variety at our location in Southern California by means of budding and find its qualities apparently are permanent.

The accompanying illustration shows in black and white a young specimen of my new variety. This plant was about six feet in height when photographed, this height representing a top growth of only five months with complete size not having been attained at that time.

In the following detailed description, color plate designations indicate Ridgway's Color Standards and Nomenclature. Other color nomenclature refers to the usual dictionary meaning of the term:

THE PLANT

Type: Climbing hybrid tea.
Growth habit: Strong grower, with climbing habit.
Blooming habit: Very floriferous, producing flowers continuously for a long season.
Stems: Medium strength; light green with red tinge.
*Thorns.*—Quantity average; red-tinged; sharp-pointed; outward-pointing; approximately ⅜ inch in length.

Foliage:
*Type.*—Pinnately compound, with 5 to 7 leaflets.
*Quantity.*—Average to abundant.
*Leaflets.*—Long oval with sharp apex. Terminal leaflet approximately 2 inches long by 2½ inches wide.
*Stipules.*—Long; very prominent.

THE FLOWER

Bud:
*Size.*—Averages 1½ inches long, opening wide.
*Form.*—Ovoid.
*Color.*—Light golden, tinted light red.
*Peduncle.*—Rigid; about 2 inches long.
*Sepals.*—Medium length; overlapping; simple except for branching ends; reflex early.

Bloom:
*Size.*—Averages 4 inches in diameter when fully open.
*Form.*—Compressed; petals roll gently backward.
*Petals.*—Ovate to orbicular.
*Petalage.*—Usually has 50 to 60 petals.
*Color.*—Golden orange, with pink shadings particularly on edges of petal. Predominating color is not shown in Ridgway's but lies between Buff Yellow (Plate IV) and Deep Chrome (Plate III). The pink shadings range from Safrano Pink (Plate II) to Eosine Pink (Plate I).

Longevity: Good both on plant and as cut flower.
Fragrance: Slight.
Reproductive organs:
*Stamens.*—Many, with red filaments and prominent golden yellow anthers.
*Pistils.*—Low and conical.

Having thus disclosed my discovery, I claim:

The new and distinct variety of hybrid tea rose plant, essentially like its parent with its combination of strong growth, prolific flower production and flowers of golden yellow with pink shadings, but characterized as to novelty by its climbing habit as shown and described.

No references cited.